United States Patent [19]

de Winter

[11] 4,223,030
[45] Sep. 16, 1980

[54] NOVEL DELTA 4,9 PREGNANA DERIVATIVES

[75] Inventor: Max S. de Winter, Oss, Netherlands

[73] Assignee: Akzona Incorporated, Asheville, N.C.

[21] Appl. No.: 942,594

[22] Filed: Sep. 15, 1978

[30] Foreign Application Priority Data

Sep. 26, 1977 [NL] Netherlands ......................... 7710462

[51] Int. Cl.$^3$ ...................... A61K 31/56; C07J 17/00; C07J 7/00
[52] U.S. Cl. .................................. 424/242; 260/397.3; 260/397.1; 260/397.4; 260/397.47
[58] Field of Search ......................... 260/397.3, 397.47

[56] References Cited

U.S. PATENT DOCUMENTS 3,277,122  10/1966  Alvarez ............................. 260/397.3

Primary Examiner—Elbert L. Roberts

Attorney, Agent, or Firm—Robert H. Falk; Charles A. Wendel; Francis W. Young

[57] ABSTRACT

New and useful steroids of the pregnane series and compositions therefor are disclosed of the formula:

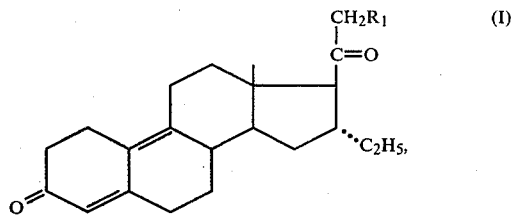

wherein $R_1$ is selected from the group consisting of H, F, OH, and $OR_2$, and $R_2$ is carbacyl of one to eighteen carbon atoms, which steroids exhibit useful pharmacological utility, to wit, progestational and/or ovulation-inhibiting activity.

11 Claims, No Drawings

NOVEL DELTA 4,9 PREGNANE DERIVATIVES

BACKGROUND TO THE INVENTION

1. Field of the Invention

The invention relates to the field of pregnane derivatives having progestational and/or ovulation-inhibiting activity, and to compositions containing same in a form suitable for therapeutic administration.

2. Description of the Prior Art and Other Information

The compounds of the invention are structurally related to the pregnane compounds of U.S. Pat. No. 3,631,077 to Zeelen et al. (19-nor-pregnanes having progestative, ovulation-inhibiting activity); U.S. Pat. No. 3,862,194 (alkylated steroids of the pregnane series for treatment of inflammatory conditions); U.S. Pat. No. 3,947,478 (alkylated steroids of the pregnane series for treatment of inflammatory conditions); U.S. Pat. No. 4,031,075 to Woods et al.(21-alkylated steroids of the pregnane series for the treatment of inflammatory conditions especially those associated with the skin and allergic reactions); U.S. Pat. No. 3,528,999 (16,17-(substituted methylene)-20-oxygenated steroids of the pregnane series).

SUMMARY OF THE INVENTION

New and useful steroids of the pregnane series ($\Delta^{4,9}$-pregnadienes) and compositions therefor are disclosed of the formula

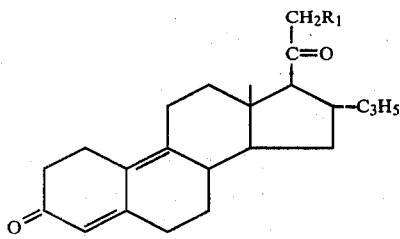

wherein $R_1$ is selected from the group consisting of H, F, OH and $OR_2$, and $R_2$ is carbacyl of one to eighteen carbon atoms, which steroids show remarkable and potent progestational and/or ovulation- inhibiting activity, especially oral progestational activity. Preferably, $R_1$ is not H. The invention also relates to a process for the preparation of pharmaceutical formulations with progestational and/or ovulation-inhibiting activity, by providing one or more of the novel steriods according to the above formula in a suitable form for therapeutic administration in unit dosage form, and to shaped objects which are obtained by this process. A method for preventing pregnancy in humans is disclosed, which comprises administering orally, in unit dosage form, a pharmaceutical composition of I in the range of about 0.05 to 2.5 mg per day, or parenterally a pharmaceutical composition containing 21-esters (I) in an amount of 5–50 mg.

DESCRIPTION OF THE PREFERRED EMBODIMENTS

The novel compounds may be prepared in ways known to those skilled in the art.

It is, for example, possible to prepare a compound of formula I by starting from the corresponding 10-carboxy-$\Delta^4$-3-ketone (II), which is reacted with iodine or bromine, preferably iodine, in the presence of a suitable heterocyclic tertiary amine(s) known to those in the art with aromatic character. This reaction is generally conducted at an elevated temperature (between about 35° C. and about 180° C.) such that the 10-carboxyl group is removed and a double bond is simultaneously created in the 9(10) position.

Examples of suitable heterocyclic tertiary amines with aromatic character are pyridine, α-collidine, β-collidine, γ-collidine, 2,4-lutidine, 2,6-lutidine, 3,4-lutidine, quinoline, isoquinoline, α-picoline, β-picoline, γ-picoline. Pyridine is a most preferably used amine. The amount of tertiary amine must be sufficient (i.e., effective) to dissolve completely the steroid used as starting material, and depends upon the 10-carboxy-$\Delta^4$-3-ketone and tertiary amine selected, but is within determination by those in the art.

If desired, other inert organic diluents or solvents may be present, such as benzene, toluene, xylene, methylene dichloride carbon tetrachloride, chlorobenzene and similar.

The amount of iodine or bromine to be used is about 1 mole-equivalent per mole-equivalent steriod (II), whereby the amount taken is generally between 1.0 and 1.1 mole-equivalents per mole-equivalent steriod (II). In lieu of molecular iodine or bromine, iodine- or bromine-releasing agents may also be used, such as N-iodo-acetamide, N-iodo-succinimide, trimethylammonium iodide-periodide, pyridine-periodide-hydro-iodide, or the corresponding bromo-compounds.

Examples of suitable starting materials (II) are: 10β-carboxy-16α-ethyl-$\Delta^4$-pregnen-3,20-dione, 10β-carboxy-16α-ethyl-21-hydroxy-$\Delta^4$-pregnen-3,20-dione, 10β-carboxy-16α-ethyl-21-acyloxy-$\Delta^4$-pregnen-3,20-dione, 10β-carboxy-16α-ethyl-21-fluoro-$\Delta^4$-pregnen-3,20-dione.

The starting materials (II) may be prepared from the corresponding 3β-hydroxy-5α-bromo-6β,19-epoxy compounds (III), which are formed as intermediates in known processes for preparing a 19-nor-pregnane compound from a pregnane compound, as is revealed, for example, in the British Patent Specification No. 1,257,522, Example VI, which is incorporated herein by reference. Such 3β-hydroxy-5α-bromo-6β,19-epoxy-pregnane derivatives are first oxidized to the corresponding 3-oxo-$\Delta^4$-6β,19-epoxides, for example, with chromic acid. The epoxide ring is then subjected to reductive opening, for example, by treatment with zinc/acetic acid in iso-propanol followed by treatment with dilute sulphuric acid, such that 3-oxo-$\Delta^4$-19-hydroxy-pregnane derivatives are obtained. These latter compounds are finally oxidized, for example, with chromic acid in acetone, to the desired 3-oxo-$\Delta^4$-10β-carboxy compounds.

After the reaction of the 10β-carboxy steroid with iodine, bromine or an iodine- or bromine-releasing agent, the 21-substituent in the thus obtained $\Delta^{4,9}$-pregnadiene derivative according to the invention may, if desired, be modified or even be introduced. A 21-OH group, a 21-ester group or a 21-fluorine (21-F) group may be introduced in various ways, and a 21-OH group present may be converted into a 21-F group. See, for example, the British Patent Specification No. 1,257,522.

A 21-hydroxy group may be esterified by reaction with an organic carboxylic acid or a functional derivative thereof, such as the acid chloride or the acid anhydride.

The carbacyl group (1-18C) optionally present at position 21 may be derived from suitable carbacylic acids, for example, acetic acid, propionic acid, butyric acid, valeric acid, oenanthic acid, capric acid, undecanoic acid, lauric acid, palmitic acid, undecenoic acid, oleic acid, trimethylacetic acid, cyclopentyl-carboxylic acid, cyclohexylacetic acid, phenylpropionic acid, benzoic acid, cyclo-octylacetic acid, phenoxyacetic acid, and adamantane-carboxylic acid. The carbacyl group is preferably unsubstituted.

The new compounds may, generally after mixing with suitable excipients and, if desired, with other active agents, be administered parenterally or enterally, in particular by the oral route, in the form of solutions, suspensions, emulsions or solid pharmaceutical formulations such as tablets, pills, capsules, dragees, suppositories and suchlike well known to those in the art.

The pharmaceutically effective amount for daily administration lies in the range from about 0.05 to about 2.5 mg. Oral administration in unit dosage form is preferred, and most preferably, one unit per day. The 21-esters (I) are also suited for serving as long-acting contraceptives for parenteral administration (depot of 5–50 mg in oil).

Preparation of starting materials; examples (a) 58.3 ml 4 N chromic acid was added at 40° C. to a solution of 15.5 g 3$\beta$-hydroxy-5$\alpha$-bromo-6$\beta$,19-oxido-16$\alpha$-ethyl-pregnan-20-one in 180 ml chloroform with stirring over a thirty-minute period. The mixture was stirred for a further 4½ hours at 40° C., after which it was cooled to room temperature (about 25° C.) and 77.5 ml water was added. The organic layer was separated and the aqueous layer was extracted twice with chloroform. 4.65 g NaHCO$_3$, 1.55 g Na$_2$SO$_4$ and 6.2 ml pyridine were added to the combined chloroform layers, after which the salts were removed by filtration at the pump and the chloroform solution remaining was evaporated to dryness. The residue was chromatographed (toluene/ethyl acetate, 6:4) and the product thus obtained was crystallized from di-isopropyl ether/hexane, giving 9.2 g 6$\beta$,19-oxido-16$\alpha$-ethyl-$\Delta^4$-pregnen-3,20-dione, melting point 123°–126° C., $[\alpha]_D^{20} = -44.3°$ (in Ch$_2$Cl$_2$).

In a similar way, 3$\beta$-hydroxy-5$\alpha$-bromo-6$\beta$,19-oxido-16$\alpha$-ethyl-21-fluoro-pregnan-20-one (obtained from 3$\beta$-hydroxy-5$\alpha$,21-dibromo-6$\beta$,19-oxido-16$\alpha$-ethyl-pregnan-20-one by the action of silver fluoride in acetonitrile) and 3$\beta$,21-dihydroxy-5$\alpha$-bromo-6$\beta$,19-oxido-16$\alpha$-ethyl-pregnan-20-one were converted into 6$\beta$,19-oxido-16$\alpha$-ethyl-21-fluoro-$\Delta^4$-pregnen-3,20-dione and 6$\beta$,19-oxido-16$\alpha$-ethyl-21-hydroxy-$\Delta^4$-pregnen-3,20-dione.

(b) 10 g zinc powder and 5 g 6$\beta$,19-oxido-$\neq\alpha$-ethyl-$\Delta^4$-pregnen-3,20-dione were suspended in a mixture of 40 ml isopropanol and 10 ml water. The mixture was refluxed in a nitrogen atmosphere and 42 ml acetic acid was added dropwise during a 15 minute period, after which the mixture was refluxed for a further hour. Zinc was removed by vacuum filtration through Hyflo$^{TM}$ (Johns Manville Co., Denver Col.) diatomaceous earth; the filtercake was washed with warm isopropanol/water 5:1 by weight. After cooling to 30° C., 4.2 ml concentrated sulphuric acid in 15 ml water was added to the reaction mixture, ensuring that the temperature was kept below 40° C. After stirring for about one hour, the pH was adjusted to about 5 with dilute sodium hydroxide, the isopropanol was removed by distillation, and the precipitate was filtered off and washed with water until neutral. Chromatography (toluene/acetone, 1:1) and crystallization from acetone gave 3 g 16$\alpha$-ethyl-19-hydroxy-$\Delta^4$-pregnen-3,20-dione (melting point 177°–178° C., $[\alpha]_D^{20} = +147°$ in CH$_2$Cl$_2$).

In a similar way, 6$\beta$,19-oxido-16$\alpha$-ethyl-21-fluoro-$\Delta^4$-pregnen-3,20-dione and 6$\beta$,19-oxido-16$\alpha$-ethyl-21-hydroxy-$\Delta^4$-pregnen-3,20-dione-21-acetate (obtained by acetylation of the corresponding 21-hydroxy compound) were converted into 16$\alpha$-ethyl-19-hydroxy-21-fluoro-$\Delta^4$-pregnen-3,20-dione (melting point 194°–198° C., $[\alpha]_D^{20} = +129°$ C. (in CH$_2$Cl$_2$) and 16$\alpha$-ethyl-19,21-dihydroxy-$\Delta^4$-pregnen-3,20-dione-21-acetate.

(c) 6 ml 8 N chromic acid was added under nitrogen and at a temperature below 15° C. to a solution of 2 g 16$\alpha$-ethyl-19-hydroxy-$\Delta^4$-pregnen-3,20-dione in 70 ml acetone. After stirring for 2 hours at room temperature 4.8 ml methanol was added dropwise to the reaction mixture.

After stirring for a further hour, the chromium salts were filtered off at the pump and the reaction mixture was poured into 500 ml water. The aqueous mixture was extracted with methylene chloride and the extract was washed with cold 2 N sodium hydroxide. The alkaline layer was washed with toluene/ether 1:1 and subsequently acidified with acetic acid to pH 4.5. Extraction with methylene chloride, washing the extract with water, drying over sodium sulphate, evaporation of the extract to dryness and chromatography of the residue (toluene/acetone 1:1) gave 1.15 g 10$\beta$-carboxy-16$\alpha$-ethyl-$\Delta^4$-pregnen-3,20-dione, melting point 111°–115° C. (decomposition), $[\alpha]_D^{20} = +202°$ (in CH$_2$Cl$_2$).

In a similar way, 16$\alpha$-ethyl-19-hydroxy-21-fluoro-$\Delta^4$-pregnen-3,20-dione and 16$\alpha$-ethyl-19,21-dihydroxy-$\Delta^4$-pregnen-3,20-dione-21-acetate were converted into 10$\beta$-carboxy-16$\alpha$-ethyl-21-fluoro-$\Delta^4$-pregnen-3,20-dione and 10$\beta$-carboxy-16$\alpha$-ethyl-21-hydroxy-$\Delta^4$-pregnen-3,20-dione.

EXAMPLE I 0.68 g iodine in 6 ml pyridine was added dropwise with stirring to a solution of 1 g 10$\beta$-carboxy-16$\alpha$-ethyl-$\Delta^4$-pregnen-3,20-dione in 10 ml pyridine. The mixture was stirred at 40° C. under nitrogen for about 2½ hours, after which it was poured into water, acidified with hydrochloric acid and extracted with methylene chloride. The extract was washed with water, dried over sodium sulphate, boiled with Norit activated charcoal (Anend Drug and Chemical Co., Inc., New York, N.Y.), filtered through Hyflo$^{TM}$ and finally evaporated to dryness. The residue was crystallized from ether. Yield 0.5 g 16$\alpha$-ethyl-$\Delta^{4,9}$-pregnadien-3,20-dione (melting point 98.0°–98.5° C., $[\alpha]_D^{20} = -196°$ in CH$_2$Cl$_2$).

EXAMPLE II

A mixture of 3.6 g iodine and 36 ml pyridine was added with stirring under a nitrogen atmosphere to a solution of 5.50 g 10$\beta$-carboxy-16$\alpha$-ethyl-21-fluoro-$\Delta^4$-pregnen-3,20-dione in 55 ml pyridine. The mixture was heated with stirring at about 110° C. for about 5 minutes, after which it was poured into 350 ml iced water. After acidification with 750 ml 2 N hydrochloric acid, the mixture was extracted with methylene chloride. The extract was washed with a 5% solution of sodium thiosulphate, followed by water until neutral, after which it was dried over sodium sulphate. The dried extract was boiled with salt, filtered through Hyflo$^{TM}$, and evaporated to dryness. Chromatography of the residue (hexane/ethylacetate 7:3 by weight) and crystallization from di-ethyl ether gave 2.2 g 16$\alpha$-ethyl-21- fluoro-Δ$^{4,9}$pregnadien-3,20-dione (melting point 104°-105° C., [α]$_D^{20}$=−160° in CH$_2$Cl$_2$).

EXAMPLE III

Under the same conditions and in a corresponding manner as in Example II, 5.47 g 10β-carboxy-16α-ethyl-21-hydroxy-Δ$^4$-pregnen-3,20-dione in 55 ml pyridine was reacted with 3.6 g iodine in 36 ml pyridine. Working up the reaction mixture yielded 1.5 g 16α-ethyl-21-hydroxy-Δ$^{4,9}$-pregnadien-3,20-dione (melting point 147°-148° C.; [α]$_D^{20}$=−167.7° in dioxane).

EXAMPLE IV

A solution of 1.9 ml dodecanoyl chloride in 7 ml acetone was added dropwise at −10° C. under a nitrogen atmosphere to a stirred solution of 1.6 g 16α-ethyl-21-hydroxy-Δ$^{4,9}$-pregnadien-3,20-dione in 6 ml pyridine and 2 ml acetone. After stirring stirring for 16 hours at 0°-5° C., 3.5 ml pyridine and 7 ml water were added and the whole was stirred for a further 1 hour at about 0° C. The reaction mixture was then stirred for 2 hours at about 45° C., after which it was poured into 200 ml iced water and extracted with diethyl ether. The extracts were washed consecutively with 15 ml 2 N sulphuric acid, four times with 10 ml cold 0.5 N sodium hydroxide solution and finally with water until neutral. Drying over Na$_2$SO$_4$ and evaporating to dryness gave 2.3 g of a residue which, when chromatographed on 100 g silica with hexane/ethyl acetate 9:1, gave 2.0 g 16α-ethyl-21-hydroxy-Δ$^{4,9}$-pregnadien-3,20-dione-21-dodecanoate (oil with [α]$_D^{20}$=−83.8° in dioxane). The 21-heptanoate, the 21-cyclo-octylacetate and the 21-decanoate were prepared in a corresponding fashion.

EXAMPLE V (a) 0.15 ml methane-sulphonyl chloride was added dropwise at −20° C. under nitrogen to a stirred solution of 0.42 g 16α-ethyl-21-hydroxy-Δ$^{4,9}$-pregnadien-3,20-dione in 4.2 ml dry pyridine. After stirring for 16 hours at about −20° C., the mixture was poured into 40 ml iced water. Extraction with CH$_2$Cl$_2$ the usual way gave 0.43 g of the 21-mesylate.

(b) A solution of 0.24 g dry NaI in 5 ml acetone was added at room temperature under nitrogen to a stirred solution of 0.42 g 21-mesylate in 10 ml acetone. The reaction mixture was boiled for 30 minutes, after which it was poured into 100 ml iced water. Extraction with methylene chloride and further working up gave 0.37 g of the 21-iodide.

(c) A solution of 0.34 g 21-iodide in 10 ml acetonitrile was heated under nitrogen blanket and in the dark to about 65° C. At this temperature, a suspension of 0.29 g AgF in 1.2 ml distilled water was then added. The reaction mixture was stirred at 65° C. for 24 hours. After cooling to 25° C., the silver salts were removed by filtration through Hyflo$^{TM}$. Material remaining on the filter was washed with CH$_2$Cl$_2$ and the filtrate was reduced to a bulk of about 5 ml on a rotary evaporator. After pouring into 40 ml iced water the reaction mixture was extracted with CH$_2$Cl$_2$ and the extract was worked up in the usual way, giving 0.27 g 16α-ethyl-21-fluoro-Δ$^{4,9}$-pregnadien-3,20-dione (melting point 104°-105° C., [α]$_D^{20}$=−160° in CH$_2$Cl$_2$).

It is claimed as the invention:

1. A compound of the formula:

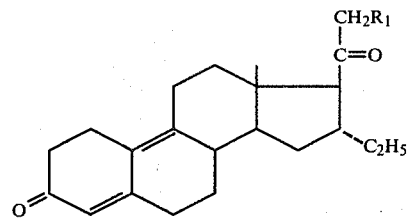

wherein R$_1$ is selected from the group consisting of F, OH and OR$_2$, and R$_2$ is carbacyl of one to eighteen carbon atoms.

2. The compound recited in claim 1 wherein R$_1$ is F.

3. The compound recited in claim 1 wherein R$_1$ is OH.

4. The compound recited in claim 1 wherein R$_1$ is OR$_2$ and R$_2$ is dodecanoyl.

5. A pharmaceutical composition having progestational ovulation-inhibiting activity comprising.

(a) a pharmaceutically effective amount of a compound of the formula

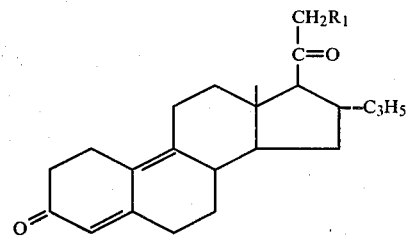

wherein R$_1$=F, OH or OR$_2$, and R$_2$ is carbacyl of one to eighteen carbon atoms and (b) a pharmaceutically effective carrier.

6. The composition recited in claim 5 wherein R$_1$ is F.

7. The composition recited in claim 5 wherein R$_1$ is OH.

8. The composition recited in claim 5 wherein R$_1$ is OR$_2$ and R$_2$ is dodecanoate.

9. A method for preventing pregnancy in humans, which comprises administering orally in unit dosage form a pharmaceutical composition comprising (a) pharmaceutically effective amount of a compound of the formula:

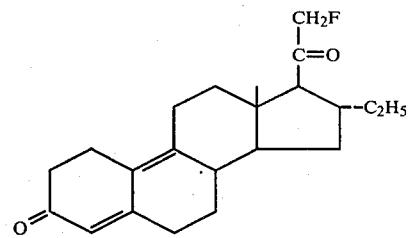

and (b) a pharmaceutically effective carrier.

10. A method for preventing pregancy in humans, which comprises administering parenterally a pharmaceutical composition comprising (a) a pharmaceutically effective amount of a compound of the formula

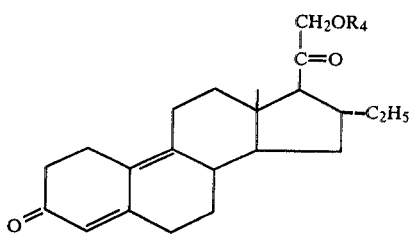
wherein $R_2$ is carbacyl of one to eighteen carbon atoms
11. The method recited in claim 10, wherein $R_2$ is dodecanoyl.
* * * * *